US 7,976,502 B2
(12) United States Patent
Baid

(10) Patent No.: US 7,976,502 B2
(45) Date of Patent: Jul. 12, 2011

(54) CATHETER INTRODUCER

(75) Inventor: Rishi Baid, New Delhi (IN)

(73) Assignee: Poly Medicure Ltd., New Delhi (IN)

( * ) Notice: Subject to any disclaimer, the term of this patent is extended or adjusted under 35 U.S.C. 154(b) by 0 days.

(21) Appl. No.: 12/437,468

(22) Filed: May 7, 2009

(65) Prior Publication Data

US 2009/0299291 A1 Dec. 3, 2009

(30) Foreign Application Priority Data

May 28, 2008 (IN) .......................... 1293/DEL/2008

(51) Int. Cl.
*A61M 5/178* (2006.01)
*A61M 5/32* (2006.01)

(52) U.S. Cl. .............. 604/164.01; 604/164.06; 604/272; 604/164.07

(58) Field of Classification Search ............. 604/164.08, 604/164.07, 164.09, 158–163
See application file for complete search history.

(56) References Cited

U.S. PATENT DOCUMENTS

| 4,964,854 | A | * | 10/1990 | Luther ...................... 604/166.01 |
| 6,117,108 | A | * | 9/2000 | Woehr et al. .................. 604/110 |
| 6,749,588 | B1 | | 6/2004 | Howell et al. |
| 2002/0169418 | A1 | * | 11/2002 | Menzi et al. ............. 604/164.07 |
| 2004/0059296 | A1 | | 3/2004 | Godfrey |
| 2004/0225260 | A1 | * | 11/2004 | Villa et al. ............... 604/164.01 |
| 2008/0249478 | A1 | * | 10/2008 | Ishikura et al. ............... 604/198 |

FOREIGN PATENT DOCUMENTS

| DE | 202 18 551 U1 | 4/2004 |
| DE | 20 2007 009 977 U1 | 11/2007 |
| EP | 0 554 841 A1 | 8/1993 |
| EP | 0 456 694 B1 | 10/1995 |
| EP | 1 604 700 A1 | 12/2005 |
| EP | 1 731 192 A2 | 12/2006 |
| EP | 1 752 188 A1 | 2/2007 |
| EP | 1 764 127 A2 | 3/2007 |
| EP | 1 974 765 A1 | 10/2008 |
| EP | 2 016 963 A1 | 1/2009 |
| GB | 2 451 153 A | 1/2009 |
| WO | WO 91/01151 A1 | 2/1991 |
| WO | WO 92/22344 A1 | 12/1992 |
| WO | WO 93/05840 A2 | 4/1993 |
| WO | WO 02/087672 A1 | 11/2002 |
| WO | WO 03/011381 A1 | 2/2003 |
| WO | WO 2004/093961 A1 | 11/2004 |

(Continued)

*Primary Examiner* — Nicholas D Lucchesi
*Assistant Examiner* — Leah Stohr
(74) *Attorney, Agent, or Firm* — Kilpatrick Townsend & Stockton LLP

(57) ABSTRACT

The invention relates to a catheter introducer comprising: a tube-like introducer sheath; an introducer hub having a distal section and a proximal section, wherein the distal section is joined to the proximal end of the introducer sheath and the proximal section defines a chamber; a needle extending through the introducer hub and the introducer sheath and having opposite proximal and distal ends, the distal end forming a needle tip; a needle hub attached to the proximal end of the needle; and a needle safety device slidably arranged on the needle, wherein the needle safety device is retained in the chamber of the introducer hub when the needle extends through the introducer hub and the introducer sheath, and is removable from the introducer hub once the needle tip is received in the needle safety device upon withdrawal of the needle from the introducer sheath.

20 Claims, 5 Drawing Sheets

FOREIGN PATENT DOCUMENTS

| | | |
|---|---|---|
| WO | WO 2005/042080 A1 | 5/2005 |
| WO | WO 2005/046750 A2 | 5/2005 |
| WO | WO 2006/023280 A2 | 3/2006 |
| WO | WO 2008/021132 A1 | 2/2008 |

* cited by examiner

Fig. 3
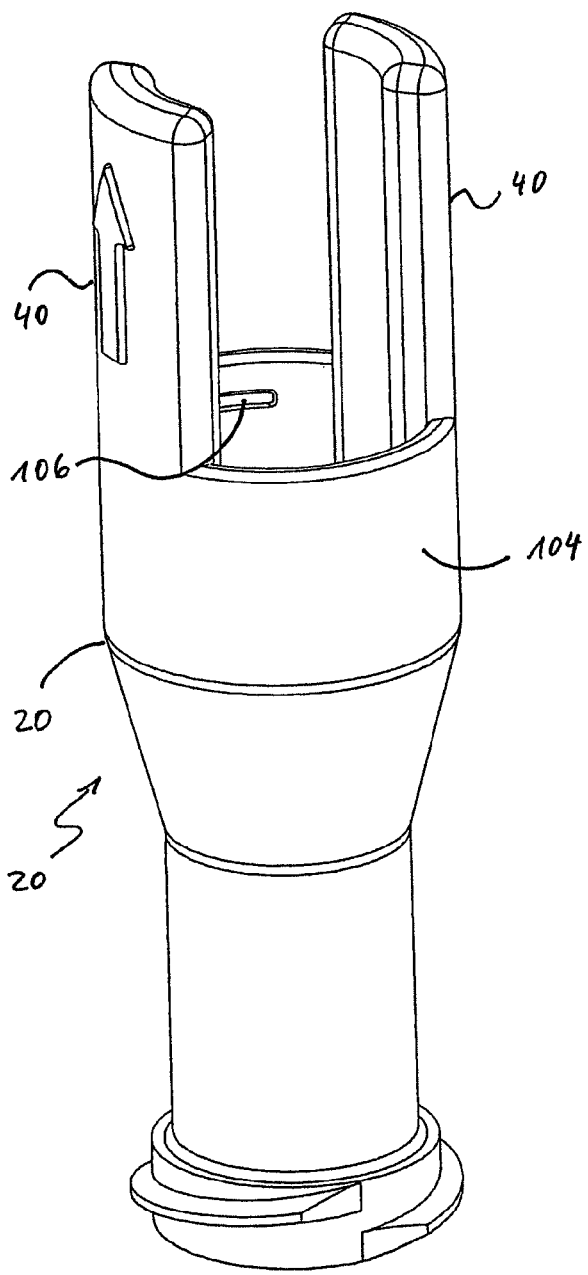
(a)
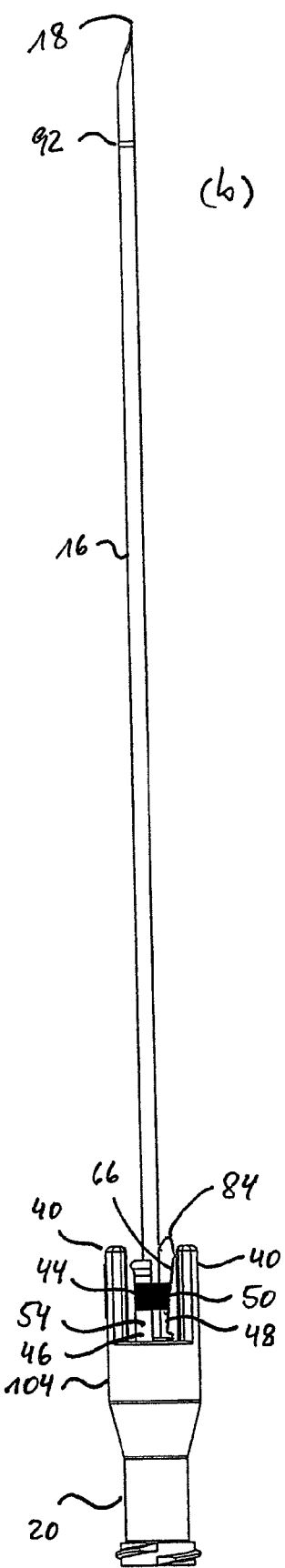
(b)

Fig. 4
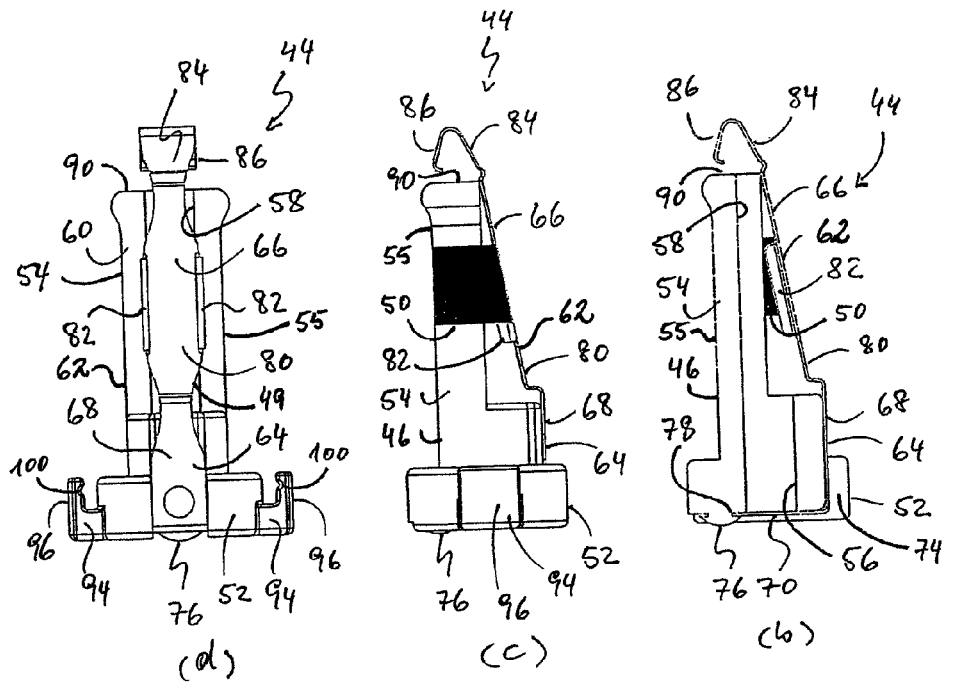
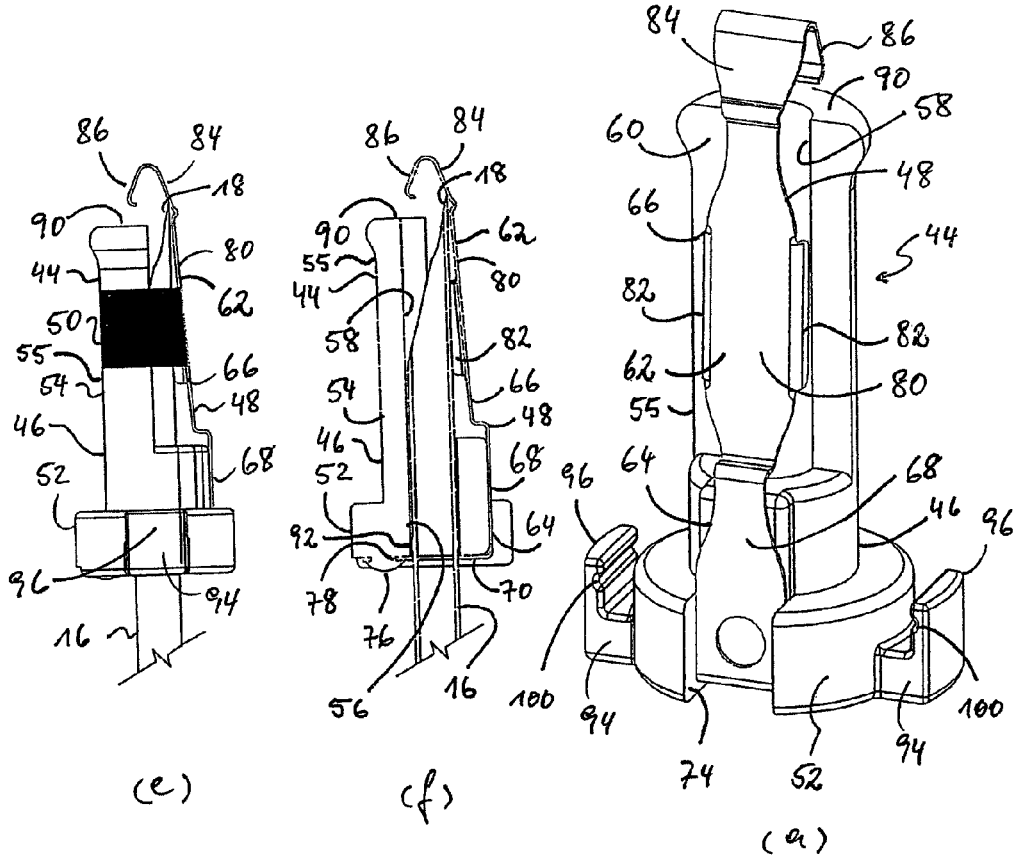

Fig. 5
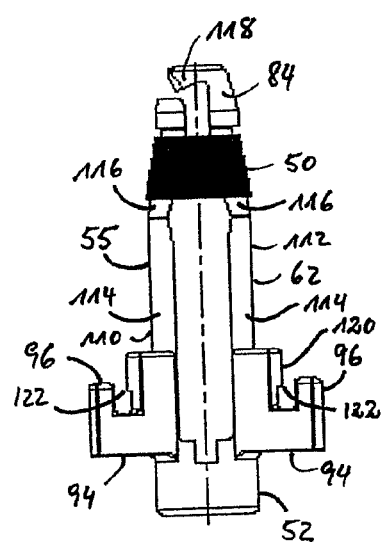
(d)
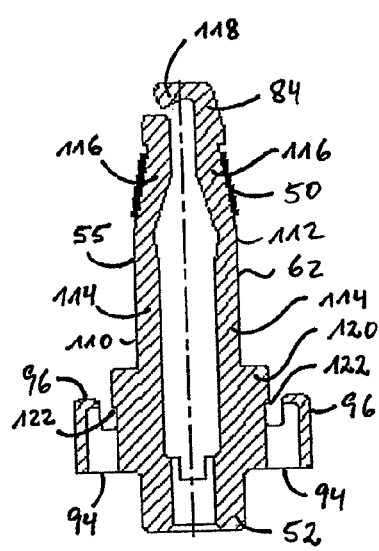
(c)
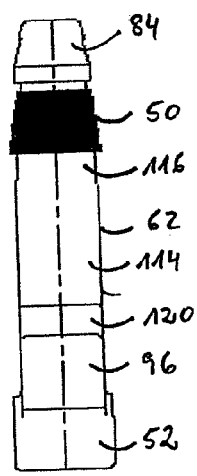
(b)
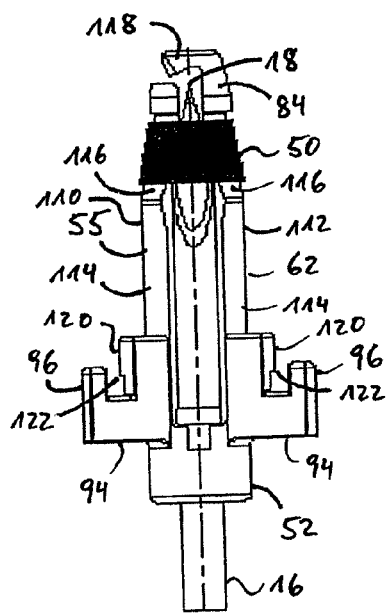
(e)
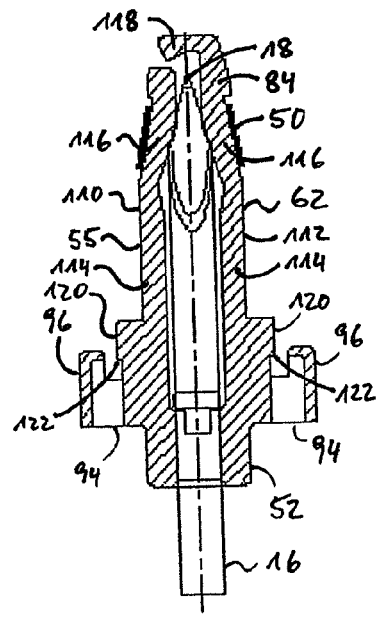
(f)
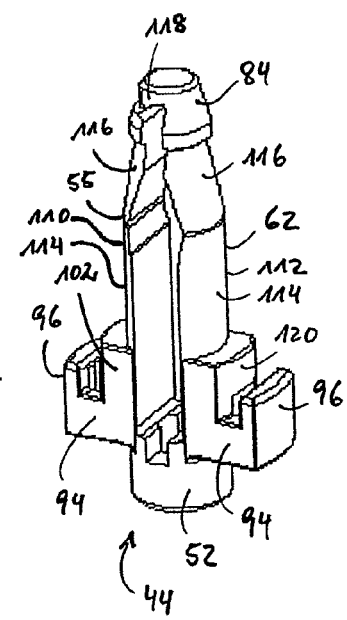
(a)

CATHETER INTRODUCER

CROSS-REFERENCE TO RELATED APPLICATION

This application claims priority to India Application No. 1293/DEL/2008, filed May 28, 2008, the disclosure of which is incorporated herein by reference.

BACKGROUND OF THE INVENTION

The present invention relates to a catheter introducer, in particular an over-the-needle peel-away catheter introducer, comprising a tube-like introducer sheath; an introducer hub having a distal section and a proximal section, wherein the distal section is joined to a proximal end of the introducer sheath and the proximal section defines a chamber; a needle extending through the introducer hub and the introducer sheath and having opposite proximal and distal ends, wherein the distal end forms a needle tip; and a needle hub attached to the proximal end of the needle.

As used herein, the term "proximal" refers to a location on the device closest to, for example, a clinician using the device. Conversely, the term "distal" refers to a location on the device farthest from the clinician, such as the distal needle tip to be inserted into a patient's vein.

A catheter introducer of the above kind is generally known and typically used to facilitate insertion and placement of a catheter or another medical device into a patient's vasculature. A conventional peel-away catheter introducer, which is also referred to as a peelable or splittable or a tear-away catheter introducer, comprises a pair of wings extending transversely from the introducer hub.

When using the peel-away catheter introducer a clinician grabs the needle hub along with the introducer hub and inserts the distal portions of the needle and of the introducer sheath at a selected site into a patient's skin. The clinician advances the device until venipuncture has been confirmed, for example, when blood enters a flashback chamber formed in the needle hub. After venipuncture has been confirmed, the clinician advances the distal end portion of the introducer sheath into the patient's vein and withdraws the needle. With the catheter introducer properly placed, the clinician can then insert a medical device, such as a catheter, into the proximal opening of the introducer sheath and advance the medical device through the introducer sheath until it is properly placed in the patient's vasculature. After placement of the medical device the clinician withdraws the introducer sheath out of the venipuncture site. The clinician then splits the introducer hub and introducer sheath into two respective separate halves by a combination of twisting and/or pulling apart of the wings along tear lines provided in the introducer hub and introducer sheath until the two halves of the introducer hub and introducer sheath split apart. The clinician can thus remove the introducer hub and introducer sheath while the catheter inserted into the patient's vein remains in place.

Due to the increasing incidence of blood-borne pathogens such as human immunodeficiency virus (HIV), hepatitis B virus (HBV) and hepatitis C virus (HCV) there is a need to protect clinicians or other medical professionals or personnel handling catheter introducers from accidental contact with the sharp needle tip after withdrawal of the needle from the introducer sheath and introducer hub.

SUMMARY OF THE INVENTION

It is an object of the present invention to provide a catheter introducer which provides reliable protection against accidental pricking by the needle once the needle has been withdrawn from the introducer sheath and introducer hub.

The catheter introducer of the invention comprises a tube-like introducer sheath; an introducer hub having a distal section and a proximal section, wherein the distal section is joined to a proximal end of the introducer sheath and the proximal section defines a chamber; a needle extending through the introducer hub and the introducer sheath and having opposite proximal and distal ends, wherein the distal end forms a needle tip; a needle hub attached to the proximal end of the needle; and a needle safety device slidably arranged on the needle, wherein the needle safety device is retained in the chamber of the introducer hub when the needle extends through the introducer hub and the introducer sheath and is removable from the introducer hub once the needle tip is received in the needle safety device upon withdrawal of the needle from the introducer sheath.

The needle safety device is operative as a guard for the needle tip by automatically covering the needle tip during withdrawal of the needle from a patient and subsequently from the introducer sheath. The needle safety device thereby serves to prevent accidental pricking of, for example, a clinician by the needle tip after removal of the needle from the introducer sheath. Hence, the needle can be safely disposed of after use.

According to one embodiment, a part of the needle safety device is, seen in a radial direction, arranged between the introducer hub and the needle hub. In this way, not only a safe seat of the needle safety device in the chamber of the introducer hub but also a secure connection between the introducer hub and the needle hub are achieved prior to withdrawal of the needle from the introducer sheath. Furthermore, the arrangement of a part of the needle safety device between the introducer hub and the needle hub facilitates a correct positioning of the needle safety device in the introducer hub and thus makes the assembly and ultimately the manufacture of the catheter introducer easier and less expensive.

According to a further embodiment, the needle safety device comprises two generally L-shaped extensions formed on opposite sides of the needle safety device, preferably in the region of a proximal end thereof. Each L-shaped extension may have an axial section extending generally in an axial direction at a distance from a base portion or a reinforced jaw portion of the needle safety device. As used herein, the axial direction is defined by the longitudinal axis of the introducer sheath and of the needle extending therethrough.

Preferably, the proximal section of the introducer hub is configured to be received between the axial sections and the base portion or the reinforced jaw portions of the needle safety device.

According to a further embodiment, the proximal section of the introducer hub is formed from two opposite proximal tube sections extending in the axial direction. Similarly, the needle hub may comprise a main body and two opposite tube sections extending in the axial direction from a distal end of the main body.

Preferably, the tube sections of the needle hub are configured to engage between the proximal tube sections of the introducer hub such that the tube sections of the needle hub and the proximal tube sections of the introducer hub together form a substantially closed tube. Because of this substantially closed tube the chamber defined by the proximal section of the introducer hub is also substantially closed, such that the needle safety device received in the chamber is protected from outside influences. This helps to permanently maintain a reliable functioning of the needle safety device.

According to a further embodiment, the main body of the needle hub comprises a tube-like portion configured to receive both a base portion of the needle safety device and a portion of the proximal section of the introducer hub. In the assembled state, i.e. prior to withdrawal of the needle, the tube-like portion of the main body of the needle hub hence surrounds a part of the needle safety device as well as a part of the proximal section of the introducer hub, thereby not only protecting the needle safety device but also preventing the introducer hub and consequently the introducer sheath from accidentally splitting into halves.

According to a further embodiment, locking means are provided to hold the portion of the proximal section of the introducer hub in place between the axial sections and the base portion or the reinforced jaw portions of the needle safety device. The locking means help to secure the needle safety device at the introducer hub as long as the needle has not been fully withdrawn from the introducer sheath and the needle tip has not been received in the needle safety device. Hence, the needle can move relative to the needle safety device until the needle tip is safely received in the needle safety device. The locking means thus ensure a correct functioning of the needle safety device.

According to a further embodiment, locking means are provided to hold the proximal section of the introducer hub in place in the tube-like portion of the needle hub. The locking means ensure a safe connection between the introducer hub and needle hub and thereby prevent the needle from being accidentally withdrawn from the introducer sheath.

Preferably, both the locking means operating between the introducer hub and the needle safety device and the locking means operating between the introducer hub and the needle hub comprise a locking protrusion on the respective one part and a corresponding locking depression in the respective other part. For instance, respective locking protrusions may be provided in the region of the proximal ends of the proximal tube sections of the introducer hub, whereas corresponding grooves may be provided at the inner side of the tube-like portion of the needle hub and of the generally L-shaped extensions of the needle safety device.

The needle safety device may comprise first and second jaws extending from the base portion in a generally axial direction.

According to one embodiment, the first jaw is integrally formed with the base portion and, preferably, substantially rigid. Due to the first jaw being formed integrally with the base portion, the number of parts in the needle safety device is reduced and the simplicity thereof increased. Forming the base portion, and thus preferably also the first jaw, from a plastic material helps to reduce the costs of manufacturing the needle safety device. The first jaw being substantially rigid increases the integrity of the needle safety device. At the same time, a reliable functioning of the needle safety device can be ensured by a suitable deflectability of the second jaw.

The second jaw may include a strip of material having spring-like properties, for example a strip of sheet metal or a strip of a suitable plastic material. Because of the first and second jaws being made from two separate parts, the needle safety device can easily be adapted to needles of different thicknesses. Furthermore, due to its simple design the needle safety device and, thus, the entire catheter introducer can be manufactured at low cost. Due to its spring-like properties the second jaw may be deflected against a restoring force by the needle extending all the way through the needle safety device, such that the second jaw snaps in front of the needle tip as soon as the needle tip is moved in between the two jaws, thereby safely guarding the needle tip.

According to an alternative embodiment that can also be manufactured at low cost, the first and second jaws may be formed integrally with the base portion, wherein preferably both jaws have spring-like properties.

The second jaw may have a distal end section which extends towards the first jaw such that it sits on the needle when the needle extends through the needle safety device, thereby deflecting the second jaw outwardly against a restoring force, and blocks the needle tip from protruding from the needle safety device when the needle tip is received between the jaws, thereby safely guarding the needle tip in the needle safety device.

According to a further embodiment, an elastic element, in particular a tension ring, surrounds the first and second jaws in order to positively collapse the jaws when the needle tip is received between the jaws. Preferably, the elastic element and the jaws are configured such that the second jaw can be spread away from the first jaw against a restoring force of the elastic element in order to allow the needle to extend all the way through the needle safety device.

Due to the elastic element exerting its restoring force on the second jaw in the deflected state of the second jaw, which is the state in which the catheter introducer is typically shelved prior to use, the elastic element ensures that the spread-apart jaws will snap together and guard the needle tip upon withdrawal of the needle from the introducer sheath even after a longer shelf time, thereby continuously ensuring a correct functioning of the needle safety device. In addition, the elastic element prevents the jaws from becoming loose when the needle safety device slides along the needle, thereby further adding to a correct functioning of the needle safety device. Furthermore, the elastic element helps prevent the needle tip from protruding sideways out of the needle safety device, thereby further increasing the protective function of the needle safety device.

According to a further embodiment, the needle extends through an axial bore in the base portion of the needle safety device, wherein the cross section of the bore is adapted to the main profile of the needle, and the needle has an enlargement near the needle tip rendering the outer diameter of the needle, seen in at least one direction, greater than the diameter of the bore. The enlargement prevents the needle safety device from sliding off the needle when the needle tip is received between the jaws, thereby even further improving the protective function of the needle safety device.

Further subject matter of the invention is a needle safety device for guarding the tip of a needle of a medical apparatus, for example a catheter introducer of the above-described type or an intravenous catheter apparatus, which comprises a base portion and two jaws extending therefrom and defining an axial direction and two generally L-shaped extensions formed on opposite sides of the needle safety device, wherein each L-shaped extension has an axial section extending generally in the axial direction at a distance from the base portion or from reinforced portions of the jaws. Apart from that, the needle safety device may be configured similar to the needle safety device of the above-described catheter introducer.

BRIEF DESCRIPTION OF THE DRAWINGS

Preferred embodiments of the invention are described in the following description and in the accompanying drawings.

FIGS. 1a to 1c show (a) a first longitudinal sectional view of a catheter introducer according to the invention, (b) a second longitudinal sectional view of the catheter introducer, and (c) an enlargement of a portion of FIG. 1a;

FIGS. 3a and 3b show (a) a perspective view of a needle hub of the catheter introducer of FIG. 1 and (b) a side view of the needle hub attached to a needle;

FIGS. 4a to 4f show (a) a perspective view of a needle safety device of the catheter introducer of FIG. 1, (b) a longitudinal sectional view of the needle safety device, (c) a side view of the needle safety device, (d) a plan view of the needle safety device, (e) a side view of the needle safety device guarding the tip of a needle, and (f) a longitudinal sectional view of the needle safety device guarding the needle tip; and FIGS. 5a to 5f show (a) a perspective view, (b) a side view, (c) a longitudinal sectional view, and (d) a plan view of an alternative needle safety device for the catheter introducer of FIG. 1, and (e) a side view and (f) a longitudinal sectional view of the needle safety device guarding the tip of a needle.

DESCRIPTION OF THE PREFERRED EMBODIMENTS

Figure 1:
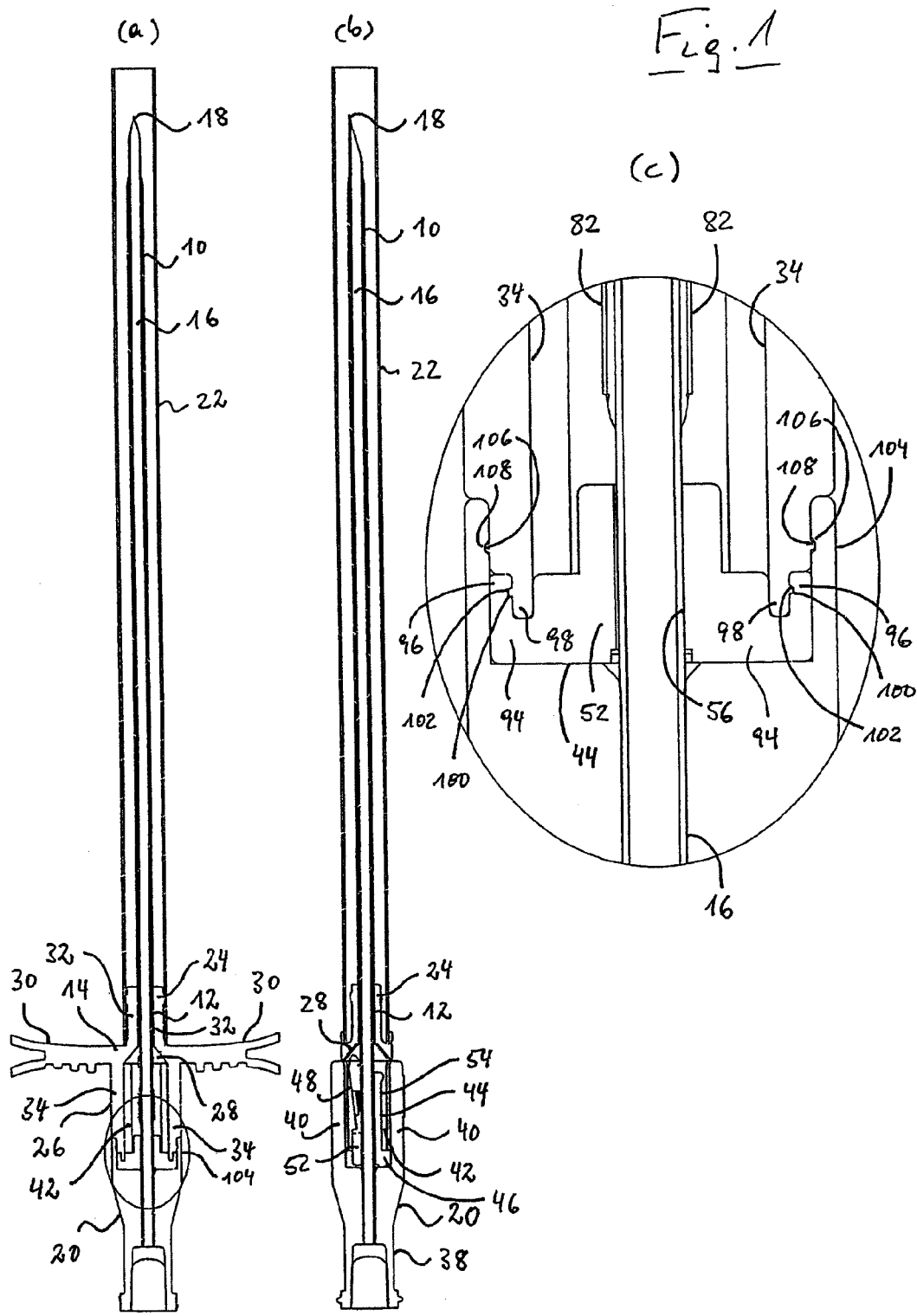

FIGS. 1a and 1b show longitudinal sectional views of an over-the-needle peel-away catheter introducer of the invention. The catheter introducer comprises a tube-like introducer sheath 10 having a proximal end region 12 that is joined to an introducer hub 14.

Furthermore, the catheter introducer comprises a needle 16 having a distal end that forms a needle tip 18 and a proximal end that is attached to a needle hub 20.

Prior to use of the catheter introducer, the needle hub 20 is connected to the introducer hub 14 such that the needle 16 extends all the way through the introducer hub 14 and the introducer sheath 10 and the needle tip 18 protrudes beyond a distal end of the introducer sheath 10.

In order to prevent accidental pricking by the needle tip 18 prior to use of the catheter introducer, an elongate cap 22 or protective tube is mounted to the introducer hub 14, which covers the length of the introducer sheath 10 and also the needle tip 18 protruding therefrom.

Figure 2:
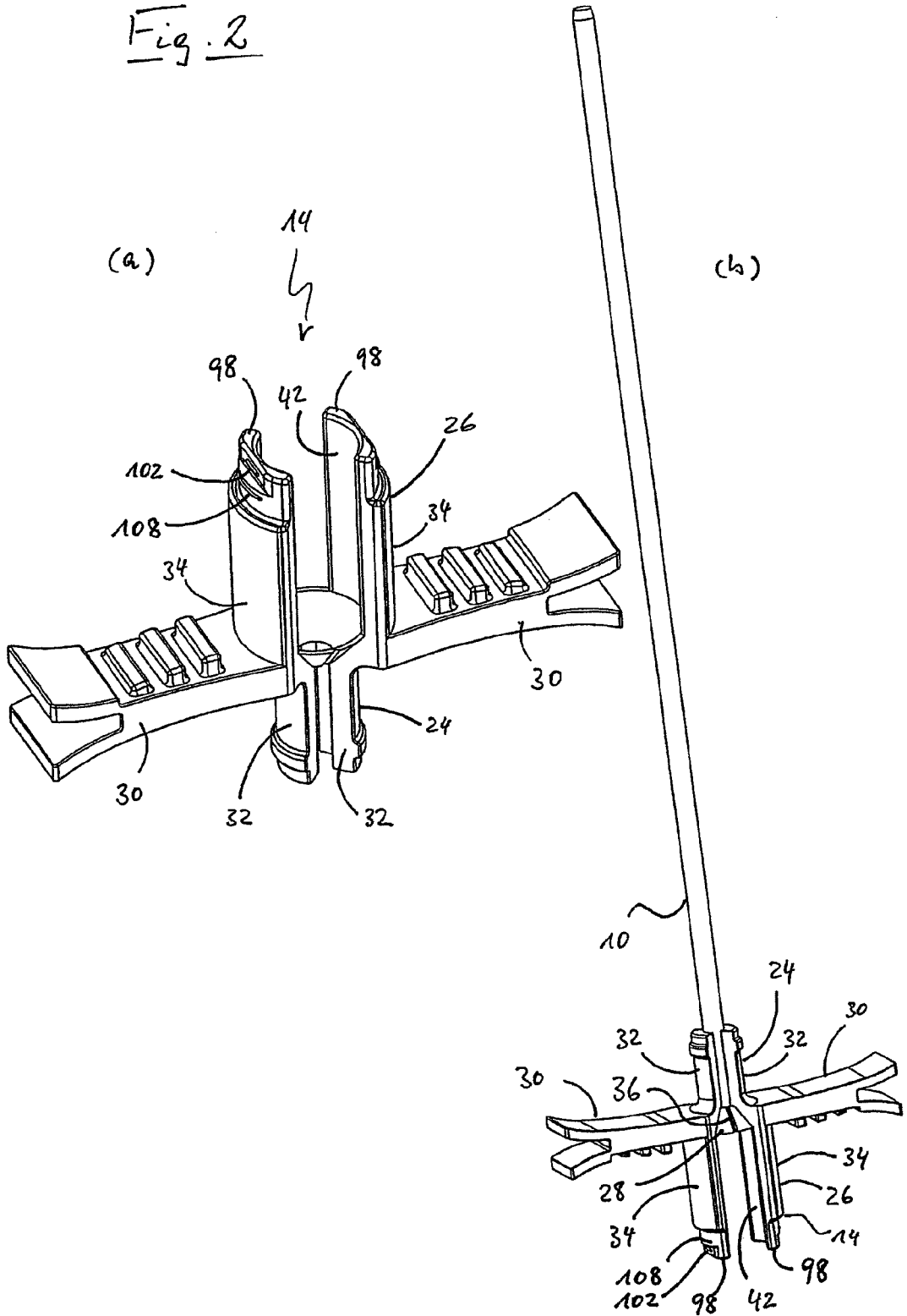
FIGS. 2a and 2b show perspective views of an introducer hub of the catheter introducer of FIG. 1 and of the introducer hub attached to an introducer sheath.

As can be seen in more detail from FIG. 2, the introducer hub 14 includes a distal section 24 and a proximal section 26. The distal section 24 has smaller inner and outer diameters than the proximal section 26 and is joined to the proximal end region 12 of the introducer sheath 10.

In the transition region between the distal section 24 and the proximal section 26 a funnel-like structure 28 is formed in the introducer hub 14, which helps to facilitate the introducing of a medical device, for example a catheter, into the introducer sheath 10 after the introducer sheath 10 has been inserted into the vein of a patient. Furthermore, two wings 30 extend transversely from the introducer hub 14 in the transition region between the distal section 24 and the proximal section 26.

Both the distal section 24 and the proximal section 26 of the introducer hub 14 are formed from pairs of opposite axially extending tube sections 32, 34 which define first and second halves of the introducer hub 14. Prior to use, the first and second halves of the introducer hub 14 are connected to each other by the funnel-like structure 28.

Once a medical device, such as a catheter, has been introduced through the introducer sheath 10 into a patient's vein, the person handling the catheter introducer, for example a clinician, withdraws the introducer sheath 10 from the venipuncture site. By a combination of twisting and/or pulling apart of the wings 30 the clinician then splits the introducer hub 14 into its two separate halves, thereby also tearing the introducer sheath 10, such that the introducer hub 14 and the introducer sheath 10 can be removed from the catheter. In order to facilitate the breaking of the introducer hub 14 into its two halves, tear lines 36 may be provided in the funnel-like structure 28 and also in the introducer sheath 10.

As can be seen in FIG. 3, the needle hub 16 comprises a main body 38 and two opposite tube sections 40 which extend in an axial direction from a distal end of the main body 38. The tube sections 40 of the needle hub 20 are configured to engage between the proximal tube sections 34 of the introducer hub 14 such that the proximal tube sections 34 of the introducer hub 14 and the tube sections 40 of the needle hub 20 form a substantially closed tube.

To this end, the tube sections 40 of the needle hub 20 and the proximal tube sections 34 of the introducer hub 14 have substantially the same length and curvature, and the tube sections 40 of the needle hub 20 have a width corresponding to the gap between the proximal tube sections 34 of the introducer hub 14.

Referring again to FIGS. 1a and 1b, the proximal tube sections 34 of the introducer hub 14 and the tube sections 40 of the needle hub 20 together form a chamber 42 for a needle safety device 44 which is slidably arranged on the needle 16.

As shown in FIG. 4, the needle safety device 44 comprises a main part 46, a clip 48 and a tension ring 50.

The main part 46 is made from a plastic material and comprises a base portion 52 and an elongate portion 54 forming a first jaw 55. The base portion 52 is of substantially cylindrical shape and has a bore 56 extending therethrough in the axial direction for receiving the needle 16.

The elongate portion 54 is of semi-cylindrical shape and extends from the base portion 52 in the axial direction. The elongate portion 52 has a groove 58 formed in its flat side 60, which extends in the axial direction along the entire length of the elongate portion 54 and forms an extension of the bore 56 in the base portion 52. While the bore 56 has a generally circular cross section that is adapted to the main outer profile of the needle 16, the groove 58 has a generally semi-circular cross section.

The clip 48 is formed from a strip of sheet metal having spring-like properties, such as steel or the like. Alternatively, the clip 48 could be formed from a plastic material which has suitable spring-like properties.

The clip 48 forms a second jaw 62 and comprises a base section 64 and a deflectable section 66. The base section 64 includes an axial section part 68 and a radial section part 70. It is adapted to engage with the base portion 52 of the main part 46 such that the axial section part 68 lies against the outer surface of the base portion 52 while the radial section part 70 lies against a rear or proximal end face of the base portion 52, when the clip 48 is attached to the main part 46. In order to ensure a correct positioning of the main part 46 and the clip 48, the base portion 52 is provided with a guide 74 for the clip 48.

The clip 48 is secured to the main part 46 by means of a heat sealing connection. To this end, the main part 46 initially has a pillar or pin 76 formed at its proximal end face and extending generally in the axial direction. The clip 48 has a corresponding opening 78 formed in its radial section part 70 for receiving the pillar or pin 76 when the clip 48 is mounted on the main part 46. Once the clip 48 has been brought into its correct position relative to the main part 46, the pillar or pin 76 extending through the opening 78 of the clip 48 is deformed by heat and/or pressure in order to increase the diameter of the pillar or pin 76. By making the diameter of the pillar or pin 76 larger than the diameter of the opening 78, the clip 48 is safely fixed at the main part 46. Alternatively, the clip 48 could be secured to the main part 46 by means of gluing or welding or any other suitable type of connection.

The base section 64 of the clip 48 passes into the deflectable section 66 via a step-like bending of the sheet metal strip. The deflectable section 66 includes a straight section part 80 which is reinforced by two elongate wings 82 that extend on either side of the straight section part 80 and are bent inwards, i.e. towards the elongate portion 54, by an angle of substantially 90°. In a relaxed state of the clip 48 mounted on the main part 46 (FIGS. 4b and 4c), the straight section part 80 does not exactly extend in the axial direction, but is bent slightly towards the elongate portion 54 of the main part 46.

In the region of its distal end, the straight section part 80 passes into a head section part 84 which extends beyond the free end of the elongate portion 54 of the main part 46. The head section part 84 has a generally V-like shape with the peak of the V pointing in the axial direction and the free leg 86 of the V extending towards the elongate portion 54.

The tension ring 50 surrounds the elongate portion 54 of the main part 46 and the straight section part 80 of the clip 48 in the region of the elongate wings 82. The tension ring 50 is made from a material having elastic properties, for example rubber. The tension ring 50 is configured so that the deflectable section 66 of the clip 48 is deflected against a restoring force of the tension ring 50, when the needle 16 extends all the way through the needle safety device 44. This situation is called the deflected state of the needle safety device 44 and is shown in FIG. 1b.

When the needle 16 does not extend all the way through the needle safety device 44 (FIGS. 4e and 4f) or when there is no needle 16 at all (FIGS. 4b and 4c), the deflectable section 66 of the clip 48 is drawn towards the elongate portion 54 of the main part 46 by the tension ring 50. In this situation, which is referred to as the collapsed state of the needle safety device 44, the head section part 84 of the clip 48 overlaps with or extends over at least a portion of the distal end face 90 of the elongate portion 54, thereby preventing the needle tip 18 from protruding out of the needle safety device 44 at the distal end thereof.

As has been mentioned above, the bore 56 provided in the base portion 52 of the main part 46 of the needle safety device 44 is adapted to the main outer profile of the needle 16. As is indicated in FIG. 3b, the needle 16 is provided with an enlargement 92 near the needle tip 18, which renders the outer diameter of the needle 16, seen in at least one direction, greater than the diameter of the bore 56. The enlargement 92 prevents the needle safety device 44 from sliding off the needle 16 when the needle tip 18 is received between the first and second jaws 55, 62 as is shown in FIGS. 4e and 4f.

As illustrated in FIGS. 4a and 4d, two generally L-shaped extensions 94 are formed on opposite sides of the needle safety device 44 in the proximal region of the base portion 52 of the main part 46. Each L-shaped extension 94 has an axial section 96 which extends in the axial direction at a distance from the base portion 52 of the needle safety device 44.

The L-shaped extensions 94 are dimensioned such that proximal end portions 98 of the proximal tube sections 34 of the introducer hub 14 are tightly received between the axial section 96 of the L-shaped extensions and the base portion 52 of the needle safety device 44 when the needle safety device 44 is received in the chamber 42 defined by the tube sections 34, 44 of the introducer hub 14 and the needle hub 20, as shown in FIGS. 1a and 1c.

In order to retain the proximal tube sections 34 of the introducer hub 14 in engagement with the L-shaped extensions 94 of the needle safety device 44, locking grooves 100 are provided in the inner surfaces of the axial sections 96 of the L-shaped extensions 94 and corresponding locking protrusions 102 are provided at the outer surfaces of the proximal tube sections 34 of the introducer hub 14 (FIGS. 1c and 2).

As is best seen in FIG. 3, the tube sections 40 of the needle hub 20 pass into a tube-like portion 104 of the main body 38 of the needle hub 20. The tube-like portion 104 is configured to receive not only the base portion 52 of the needle safety device 44 but also a part of the proximal tube sections 34 of the introducer hub 14 (FIGS. 1a and 1c).

In order to secure the proximal tube sections 34 of the introducer hub 14 in the tube-like portion 104 of the needle hub 20, locking grooves 106 are provided in the inner surface of the tube-like portion 104 of the needle hub 20 (FIG. 3) and corresponding locking protrusions 108 are formed at the outer surface of the proximal tube sections 34 of the introducer hub 14 in a distance distal from the locking protrusions 102 provided for engagement with the needle safety device 44 (FIGS. 1c and 2).

The engagement of the locking protrusions 108 with the locking grooves 106 prevents the needle hub 20 from being accidentally released from the introducer hub 14.

At the same time, the locking engagement of the locking protrusions 102 with the locking grooves 100 secures the needle safety device 44 at the introducer hub 14, thereby preventing the needle safety device 44 from being accidentally withdrawn from the introducer hub 14 before the needle tip 18 has been received between the first and second jaws 55, 62 of the needle safety device 44.

FIG. 5 shows an alternative embodiment of a needle safety device 44.

Similar to the embodiment of FIG. 4 the needle safety device 44 shown in FIG. 5 comprises a main part 46 and a tension ring 50. However, in contrast to the embodiment of FIG. 4, the needle safety device 44 shown in FIG. 5 does not have any separate clip 48. Instead, the main part 46 comprises a base portion 52 and two elongate portions 110, 112 that extend from the base portion 52 generally in the axial direction to form the first and second jaws 55, 62.

The base portion 52 and the two elongate portions 110, 112 are integrally formed and made, for example, from a plastic material. The base portion 52 is of substantially cylindrical shape and has a bore 56 extending therethrough in the axial direction for receiving the needle 16. The bore 56 has a generally circular cross section that is adapted to the main outer profile of the needle 16.

The elongate portions 110, 112 each have a proximal section 114 and a distal section 116. While the proximal sections 114 extend generally parallel to each other, the distal sections 116 are inclined towards each other in the collapsed state of the needle safety device 44 (FIGS. 5e and 5f) or when no needle 16 extends through the needle safety device 44 (FIGS. 5a to 5d).

The distal section 116 of the second jaw 62 passes into a head section part 84 which extends beyond the free end of the first jaw 55. The head section part 84 includes an end section 118 which extends in a radial direction towards the first jaw 55. The length of the end section 118 is such that it covers at least a portion of the free end of the first jaw 55 when the needle safety device 44 is in its collapsed state in order to prevent the needle tip 18 from protruding out of the needle safety device 44 (FIGS. 5e and 50.

The tension ring 50 surrounds the first and second jaws 55, 62 in the region of their distal sections 116. The tension ring 50 is made from a material having elastic properties, for example rubber. The tension ring 50 is configured so that the first and second jaws 55, 62 are deflected against a restoring force of the tension ring 50, when the needle 16 extends all the way through the needle safety device 44.

Two generally L-shaped extensions 94 are formed on opposite sides of the needle safety device 44. The L-shaped extensions 94 emerge from reinforced portions 120 of the first and second jaws 55, 62 in the proximal end region of the first and second jaws 55, 62. Each L-shaped extension 94 has an axial section 96 which extends in the axial direction at a distance from the respective reinforced portion 120.

The L-shaped extensions 94 are dimensioned such that proximal end portions 98 of the proximal tube sections 34 of the introducer hub 14 are tightly received between the axial sections 96 of the L-shaped extensions and the reinforced portions 120 of the needle safety device 44 when the needle safety device 44 is received in the chamber 42 defined by the tube sections 34, 44 of the introducer hub 14 and the needle hub 20, as shown in FIGS. 1a and 1c.

Contrary to the embodiment of FIG. 4, the L-shaped extensions 94 of the needle safety device 44 shown in FIG. 5 do not have any locking grooves 100 in the inner surfaces of the axial sections 96 of the L-shaped extensions 94. Instead, the reinforced portions 120 are provided with locking shoulders 122 for retaining the proximal tube sections 34 of the introducer hub 14 between the axial sections 96 of the L-shaped extensions and the reinforced portions 120 of the needle safety device 44. Accordingly, the proximal tube sections 34 of the introducer hub 14 should be provided with corresponding locking means at their inner surfaces, for example suitable depressions.

LIST OF REFERENCE NUMERALS 10 introducer sheath
12 proximal end region
14 introducer hub
16 needle
18 needle tip
20 needle hub
22 elongate cap
24 distal section
26 proximal section
28 funnel-like structure
30 wing
32 distal tube section
34 proximal tube section
36 tear line
38 main body
40 tube section
42 chamber
44 needle safety device
46 main part
48 clip
50 tension ring
52 base portion
54 elongate portion
55 first jaw
56 bore
58 groove
60 flat side
62 second jaw
64 base section
66 deflectable section
68 axial section part
70 radial section part
74 guide
76 pin
78 opening
80 straight section part
82 wing
84 head section part
86 free leg
90 end face
92 enlargement
94 L-shaped extension
96 axial section
98 proximal end portion
100 locking groove
102 locking protrusion
104 tube-like portion
106 locking groove
108 locking protrusion
110 elongate portion
112 elongate portion
114 proximal section
116 distal section
118 end section
120 reinforced portion
122 locking shoulder

The invention claimed is:

1. A catheter introducer comprising:
a tube-like introducer sheath;
an introducer hub having a distal section and a proximal section, wherein the distal section is joined to the introducer sheath and the proximal section defines a chamber;
a needle extending through the introducer hub and the introducer sheath and having opposite proximal and distal ends, wherein the distal end forms a needle tip;
a needle hub attached to the proximal end of the needle; and
a needle safety device slidably arranged on the needle, wherein the needle safety device is retained in the chamber of the introducer hub when the needle extends through the introducer hub and the introducer sheath, and removable from the introducer hub once the needle tip is received in the needle safety device upon withdrawal of the needle from the introducer sheath,
the needle safety device comprising first and second jaws extending from the base portion in a generally axial direction;
an elastic element comprising a tension ring and surrounding the first and second jaws in order to positively collapse the jaws when the needle tip is received between the jaws; and
two generally L-shaped extensions formed on opposite sides of the needle safety device for engagement with the introducer hub.

2. A catheter introducer in accordance with claim 1, wherein,
seen in a radial direction, a part of the needle safety device is arranged between the introducer hub and the needle hub.

3. A catheter introducer in accordance with claim 1, wherein
the L-shaped extensions are formed in the region of a proximal end of the needle safety device.

4. A catheter introducer in accordance with claim 1, wherein
each L-shaped extension has an axial section extending generally in an axial direction at a distance from a base portion or a reinforced jaw portion of the needle safety device.

5. A catheter introducer in accordance with claim 4, wherein
the proximal section of the introducer hub is configured to be received between the axial sections and the base portion or the reinforced jaw portions of the needle safety device.

6. A catheter introducer in accordance with claim 5, wherein
locking means are provided to hold the proximal section of the introducer hub in place between the axial sections and the base portion or the reinforced jaw portions of the needle safety device,
wherein the locking means comprise a locking protrusion on the respective one part and a corresponding locking depression in the respective other part.

7. A catheter introducer in accordance with claim 1, wherein
the proximal section of the introducer hub is formed from two opposite tube sections extending in an axial direction.

8. A catheter introducer in accordance with claim 1, wherein
the needle hub comprises a main body and two opposite tube sections extending in an axial direction from a distal end of the main body.

9. A catheter introducer in accordance with claim 1, wherein
the proximal section of the introducer hub is formed from two opposite tube sections extending in an axial direction and the needle hub comprises a main body and two opposite tube sections extending in an axial direction from a distal end of the main body,
wherein the tube sections of the needle hub are configured to engage between the tube sections of the introducer hub such that the tube sections of the introducer hub and the tube sections of the needle hub form a substantially closed tube.

10. A catheter introducer in accordance with claim 1, wherein
a main body of the needle hub comprises a tube-like portion configured to receive both a base portion of the needle safety device and a portion of the proximal section of the introducer hub.

11. A catheter introducer in accordance with claim 10, wherein
locking means are provided to hold the portion of the proximal section of the introducer hub in place in the tube-like portion of the needle hub.

12. A catheter introducer in accordance with claim 11, wherein
the locking means comprise a locking protrusion on the respective one part and a corresponding locking depression in the respective other part.

13. A catheter introducer in accordance with claim 1, wherein
the first jaw is integrally formed with the base portion and substantially rigid.

14. A catheter introducer in accordance with claim 1, wherein
the second jaw includes a strip of material having spring-like properties.

15. A catheter introducer in accordance with claim 14, wherein
the second jaw includes a strip of sheet metal or plastic.

16. A catheter introducer in accordance with claim 1, wherein
the first jaw and the second jaw are integrally formed with the base portion.

17. A catheter introducer in accordance with claim 16, wherein
both jaws have spring-like properties.

18. A catheter introducer in accordance with claim 1, wherein
the second jaw has a distal end section which extends towards the first jaw such that it sits on the needle when the needle extends through the needle safety device, thereby deflecting the second jaw outwardly against a restoring force, and blocks the needle tip from protruding from the needle safety device when the needle tip is received between the jaws.

19. A catheter introducer in accordance with claim 1, wherein
the needle extends through an axial bore in the base portion of the needle safety device, wherein the cross section of the bore is adapted to the main profile of the needle, and the needle has an enlargement near the needle tip rendering the outer diameter of the needle, seen in at least one direction, greater than the diameter of the bore.

20. A needle safety device for guarding the tip of a needle of a medical apparatus, comprising:
a base portion and first and second jaws extending from the base portion in a generally axial direction;
an elastic element comprising a tension ring and surrounding the first and second jaws in order to positively collapse the jaws when the needle tip is received between the jaws; and
two generally L-shaped extensions formed on opposite sides of the needle safety device, wherein each L-shaped extension has an axial section extending generally in the axial direction at a distance from the base portion or a reinforced jaw portion.

* * * * *